(12) United States Patent
Dominguez et al.

(10) Patent No.: US 6,770,082 B2
(45) Date of Patent: Aug. 3, 2004

(54) SURGICAL HEADFRAME WITH SOFT CONTACT PADS FOR USE WITH A STEREOTACTIC SYSTEM

(75) Inventors: Leonel Dominguez, Jacksonville, FL (US); Michael S. Ferrell, Orange Park, FL (US); Prasad Nalluri, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 197 days.

(21) Appl. No.: 09/961,569

(22) Filed: Sep. 24, 2001

(65) Prior Publication Data

US 2002/0042619 A1 Apr. 11, 2002

Related U.S. Application Data
(60) Provisional application No. 60/235,215, filed on Sep. 24, 2000.

(51) Int. Cl.[7] .............................................. A61B 19/00
(52) U.S. Cl. ..................................................... 606/130
(58) Field of Search ........................ 606/1, 130; 5/622; 128/97.1, 845, 857; 604/79; 348/53, 77

(56) References Cited

U.S. PATENT DOCUMENTS

| 841,714 | A | * | 1/1907 | Peters ........................ 128/97.1 |
| 937,596 | A | * | 10/1909 | Gray et al. ................. 128/97.1 |
| 999,945 | A | * | 8/1911 | Aub ............................ 607/139 |
| 4,360,028 | A | | 11/1982 | Barbier et al. |
| 4,797,736 | A | * | 1/1989 | Kloots et al. ................ 348/370 |
| 5,207,688 | A | | 5/1993 | Carol |
| 5,330,485 | A | * | 7/1994 | Clayman et al. ............. 606/130 |
| 5,387,220 | A | | 2/1995 | Pisharodi |
| 5,388,580 | A | | 2/1995 | Sullivan et al. |
| 5,412,811 | A | | 5/1995 | Hildenbrand et al. |
| 5,601,569 | A | | 2/1997 | Pisharodi |
| 5,649,936 | A | | 7/1997 | Real |
| 5,706,811 | A | * | 1/1998 | Takeda et al. ............... 600/417 |
| 5,800,352 | A | | 9/1998 | Ferre et al. |
| 6,080,164 | A | | 6/2000 | Oshio et al. |
| 6,096,048 | A | | 8/2000 | Howard, III et al. |
| 6,594,839 | B1 | * | 7/2003 | Papay ........................... 5/637 |

OTHER PUBLICATIONS

Medtronic–XoMed Brochure, "LandmarX™ ENT Image Guidance System", 14 pages; Dec. 1999.
A copy of PCT International Search Report mailed on Feb. 15, 2002 (7 pages).

\* cited by examiner

Primary Examiner—Eduardo C. Robert
(74) Attorney, Agent, or Firm—Trevor D. Arnold; Timothy A. Czaja

(57) ABSTRACT

A surgical headframe for maintaining a stereotactic system reference frame relative to a patient's head. The headframe includes a frame body, first and second arms, a plurality of contact pads, and a strap. The first and second arms extend from opposing sides of the frame body, respectively. The plurality of contact pads are coupled to the frame body and are each adapted to engage a patient's head. The strap is selectively connectible to the first and second arms. In this regard, the strap is adapted for wrapping about a back of a patient's head. The surgical headframe is capable of precisely positioning and fixating the reference frame to the patient's head daring these stereotactic procedures.

49 Claims, 7 Drawing Sheets

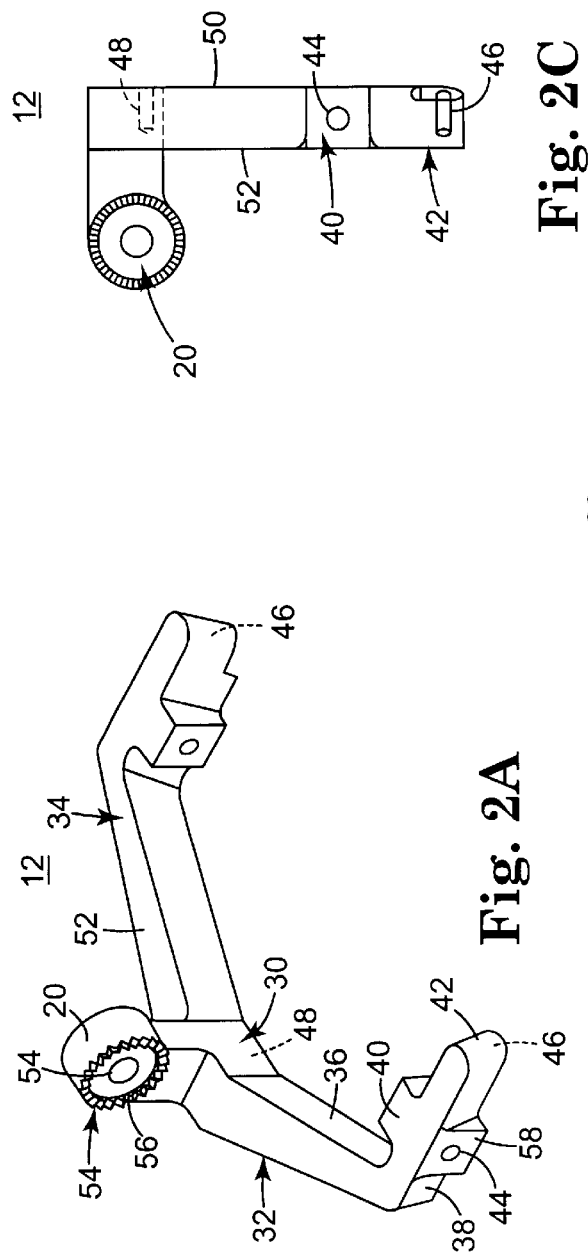
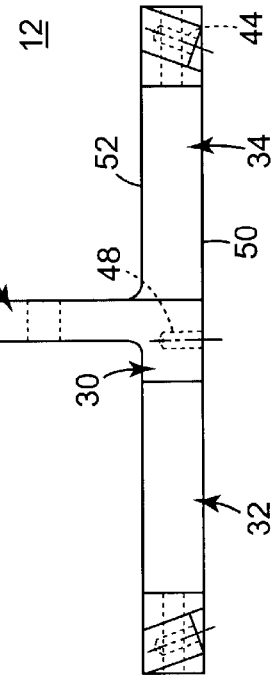
Fig. 2A
Fig. 2B
Fig. 2C

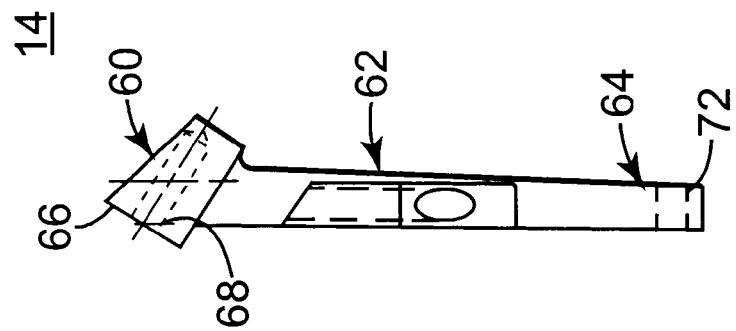
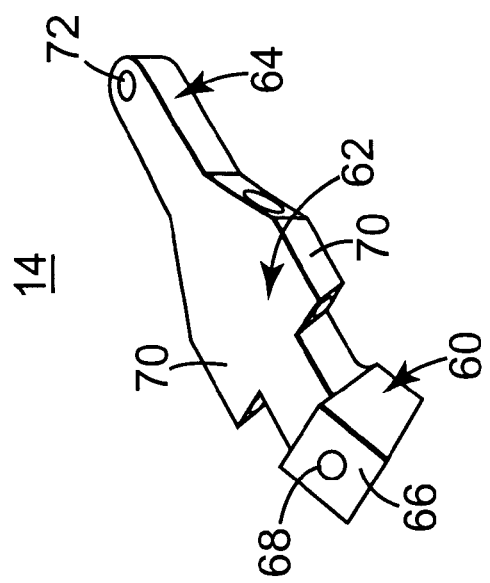

SURGICAL HEADFRAME WITH SOFT CONTACT PADS FOR USE WITH A STEREOTACTIC SYSTEM

CROSS-REFERENCE TO RELATED APPLICATIONS

This application claims the benefit, and incorporates by reference the entirety of, U.S. Provisional Application Ser. No. 60/235,215, filed Sep. 4, 2000.

BACKGROUND OF THE INVENTION

The present invention relates to a headframe for use with a stereotactic system. More particularly, it relates to a surgical headframe for accurate, non-traumatic (non-invasive) positioning (fixation) of a reference frame to a patient as part of a stereotactic system, especially a tandem optical stereotactic device.

Stereotactic surgical systems provide surgeons with visual guidance information of surgical instruments/probes relative to an enclosed anatomical position, especially within the cranium or head. Basically, a stereotactic surgical system provides a quantitative determination of an anatomical position based upon a scanned image, such as a CAT scan, MRI scan, PET scan, etc. This scanned information is processed by a computer to produce a displayable image of the head. Subsequently, during a surgical procedure, the stereotactic system relates a position of a surgical instrument otherwise deployed within the anatomical body of interest (e.g., the head) relative to the previously-generated scanned information in visual form.

Stereotactic devices are highly useful in the field of neurosurgery, and more recently ENT procedures requiring instrument deployment in close proximity to the optic nerve, carotid artery, skull base, facial nerve, internal auditory canal, etc. A more recent stereotactic system is optical or camera based in which two cameras are employed to visualize special instruments in a surgical field, digitize the viewed information from the camera and relate it via computer graphics to image data generated by the above-described image scanning techniques. The relationship of the optical camera(s) view and the image data will then make quantitative the anatomy seen in the camera view and also make quantitative the position of surgical instruments such as probes, microscopes, or space pointers, etc., relative to the anatomy via registration of the camera view to the image data. An example of such a tandem optical, stereotactic device is available under the trade name Landmar™ ENT Image Guidance System, from Medtronic-Xomed of Jacksonville, Fla.

Regardless of the exact stereotactic configuration, a stereotactic or dynamic reference frame must be fixed to the patient's head to provide accurate positioning information. A wide variety of headframes or headframes have been developed to facilitate fixation of the reference frame to the patient's head. In this regard, important constraints relating to the headframe design include precise positioning of the reference frame relative to the patient's head, relatively long-term fixation, and allowing for movement of the patient's head without deviation of a position of the reference frame relative to the head during the surgical procedure. In light of these constraints, many of the available stereotactic headframes incorporate one or more bone screws or bone pins to physically secure the headframe to the skull. Obviously, this is highly invasive, and contrary to the minimally invasive nature of intended procedures. Alternatively, other stereotactic headframes are tightly clamped to the patient's head. Due to the possibility of headframe movement along the patient's skin, the clamping device(s) is typically very rigid, again causing discomfort to the patient under extended usage.

Surgical stereotactic systems continue to rapidly evolve with improvements to imaging and display components. However, the headframe apparatus has essentially remained unchanged, and is unacceptably bulky and invasive or traumatic. Therefore, a need exists for an improved surgical headframe for use with a stereotactic system.

SUMMARY OF THE INVENTION

One aspect of the present invention provides a surgical headframe for maintaining a stereotactic system reference frame relative to a patient's head. The headframe includes a frame body, first and second arms, a plurality of contact pads, and a strap. The first and second arms extend from opposing sides of the frame body, respectively. The plurality of contact pads are coupled to the frame body and are each adapted to engage a patient's head. Finally, the strap is selectively connectible to the first and second arms. In this regard, the strap is adapted for wrapping about a back of a patient's head. With this construction, the surgical headframe is capable of precisely positioning and fixating the reference frame to the patient's head during a stereotactic procedure, without requiring bone screws, bone pins or clamps. In one preferred embodiment, three contact pads are provided, and are arranged in a tripod-like fashion. In a further preferred embodiment, the contact pads are pivotally coupled to the frame body, and are co-planer. With this preferred construction, the headframe is highly stable when applied to the patient's head. In yet another preferred embodiment, a control pad is mounted to the frame body.

Yet another aspect of the present invention relates to a method of securing a reference frame to a patient's head as part of a surgical procedure. The method includes providing a surgical headframe having a frame body, first and second arms, a plurality of contact pads, and a strap. The first and second arms extend from opposing sides of the frame body. The contact pads are coupled to the frame body. Finally, the strap is selectively securable to the first and second arms. With this in mind, the reference frame is mounted to the headframe. The headframe is then positioned at the patient's head such that the contact pads contact the patient's head. The strap is then wrapped behind the patient's head. Finally, the strap is secured to the first and second arms. In one preferred embodiment, the first and second arms are rotatably mounted to the frame body, thereby reducing moment forces generated by extension of the strap about the patient's head from being transmitted to the patient's forehead and serve to increase user comfort.

Yet another aspect of the present invention relates to a method of manufacturing a surgical headframe for use in a stereotactic procedure. The method includes providing a frame body having a central portion and opposing sides. First and second arms are extended from the opposing sides of the frame body, respectively. A plurality of contact pads are coupled to the frame body. In this regard, each of the contact pads are adapted to engage a patient's head. Finally, a strap is selectively secured to the first and second arms opposite the frame body. To this end, the strap is adapted for wrapping about a back of a patient's head. Upon final assembly, the headframe is adapted to receive and maintain a stereotactic reference frame. In one preferred embodiment, a first contact pad is coupled to the central portion of the frame body, and the second and third contact pads are positioned opposite one another relative to the first contact pad.

BRIEF DESCRIPTION OF THE DRAWINGS

FIGS. 2A–2C illustrate a frame body of the headframe of FIG. 1;

FIGS. 3A–3B illustrate a swivel arm portion of the headframe of FIG. 1;

DESCRIPTION OF THE PREFERRED EMBODIMENTS

Figure 1:
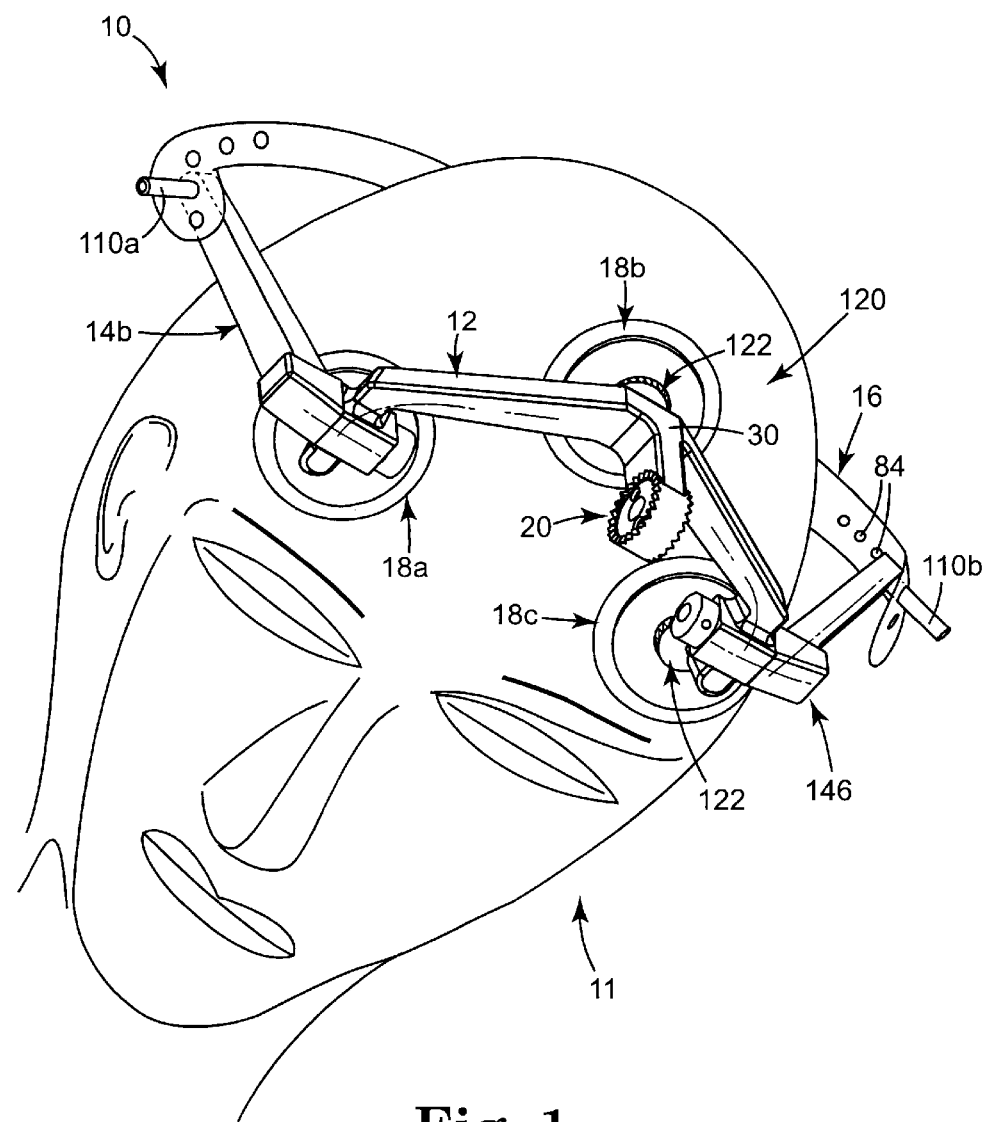
FIG. 1 is a perspective view of a surgical headframe in accordance with the present invention applied to a patient.

A preferred embodiment of a surgical headframe 10 is provided in FIG. 1 as applied to a patient 11. Although not illustrated, it will be understood that the surgical headframe 10 is for use with a stereotactic image guidance system (not shown), an example of which is available under the trade name LandmarX® from Medtronic-Xomed. With this in mind, the headframe 10 includes a head frame body 12, swivel arms 14, a strap 16, and contact pads 18a–18c. Details on the various components are provided below. In general terms, however, the head frame body 12 is configured for placement about a patient's skull. The swivel arms 14 extend from opposite sides of the frame body 12, respectively. The strap 16 is connected to, and extends between, the swivel arms 14a, 14b. Finally, the contact pads 18a–18c are secured to the frame body 12 as shown, positioned to precisely fixate the headframe 10 relative to the patient's skull. As a point of reference, and as described elsewhere, the surgical headframe 10 is preferably configured to receive and rigidly maintain a dynamic reference frame (not shown), such as at a post or lug 20 otherwise formed by the frame body 12.

The frame body 12 is shown in greater detail in FIGS. 2A–2C. The frame body 12 is preferably formed from a rigid, light-weight material, such as aluminum, and forms the post 20, a central portion 30, a first leg 32, and a second leg 34. The first and second legs 32, 34 extend in opposite directions from the central portion 30, and are preferably identical in construction. In this regard, each of the arms 32, 34 includes a first section 36 and second section 38. The first section 36 extends in an angular fashion from the central portion 30. The second section 38 extends downwardly from the first section 36 (or rearwardly relative to the orientation of FIG. 2A) and defines an arm receiving region 40 and a pad receiving region 42. The arm receiving region 40 is configured to receive a respective one of the swivel arms 14 (FIG. 1) at an engagement surface 58 via a lateral passage 44 formed therein. Similarly, the pad receiving region 42 is configured to receive a respective one of the contact pads 18 (FIG. 1) via a transverse bore 46 (best shown in FIG. 2C). Notably, and as best shown in FIG. 2B, the central portion 30 similarly forms a transverse bore 48 for mounting of one of the contact pads 18 (FIG. 1). The frame body 12 is highly planar or flat at an inner surface 50 thereof. That is to say, regardless of how the legs 32, 34 are formed relative to the central portion 30, the frame body 12 is, as a whole, planar at the inner surface 50. This preferred configuration is illustrated in FIGS. 2B and 2C. As a result, the contact pads 18, otherwise assembled to the respective passages 46, 48, are similarly oriented in a planar fashion. Further, and returning to FIG. 2A, the transverse bores 46 are equidistantly spaced relative to the central portion 30, and thus relative to the transverse bore 48 formed therein. This configuration effectively positions the subsequently assembled contact pads 18 in a triangular or tripod-type configuration relative to the frame body 12. As described in greater detail below, this tripod configuration provides increased lateral stability when the headframe 10 is secured fixed to a patient.

In one preferred embodiment, the frame body 12 has an overall width (i.e., distance between the respective second sections 38 of the legs 32, 34) of 4.125 inches and a height (i.e., distance between pad receiving region 42 and central portion 30) of 2.25 inches. These preferred dimensions correspond generally with the spacing of an adult forehead. Alternatively, however, other dimensions are equally acceptable. Finally, the post 20 extends in a perpendicular fashion (relative to the inner surface 50) from an outer surface 52. In one preferred embodiment, the post 20 includes an auxiliary frame receiving body 54 including a central passage 54 and a starburst or toothed surface 56.

One of the swivel arms 14 is shown in greater detail in FIGS. 3A and 3B. The swivel arm 14 is preferably integrally formed from a rigid, light-weight material, such as aluminum, and is defined by a base 60, an intermediate section 62, and a leading end 64. The base 60 is configured for mounting to the frame body 12 (FIG. 2) and defines an inner face 66 through which a passage 68 transversely extends. As best shown in FIG. 3B, the base 60 extends transversely relative to the intermediate section 62. In other words, the inner face 66 is non-contiguous with a corresponding surface of the intermediate section 62 such that the inner face 66 is non-planar relative to the intermediate section 62. In one preferred embodiment, relative to a plane defined by the intermediate section 62, a plane of the inner face 66 extends at an angle of approximately 32°, although other dimensions are equally acceptable. Regardless, the inner face 66 is configured to abut a corresponding surface of a respective one of the arm receiving regions 40 (FIG. 2A) previously described, for example the engagement surface 58 (FIG. 2A). The angular orientation of the inner face 66 relative to the intermediate section 62, as well as the angular extension of the intermediate section 62 relative to the base 60, facilitates extension of the swivel arm 14 along a side of a patient's head (not shown), as well as allowing the swivel arm 14 to rotate in the plane of the inner face 66.

The intermediate section 62 is depicted in FIG. 3A as including opposing shoulders 70 which are provided to receive and maintain auxiliary components (not shown). Alternatively, where the auxiliary components are unnecessary or are secured to other portions of the headframe 10, the shoulders 70 can be eliminated. Finally, the leading end 64 forms an opening 72 for receiving a pin (not shown) for securing the strap 16 (FIG. 1) to the swivel arm 14.

Figure 4:
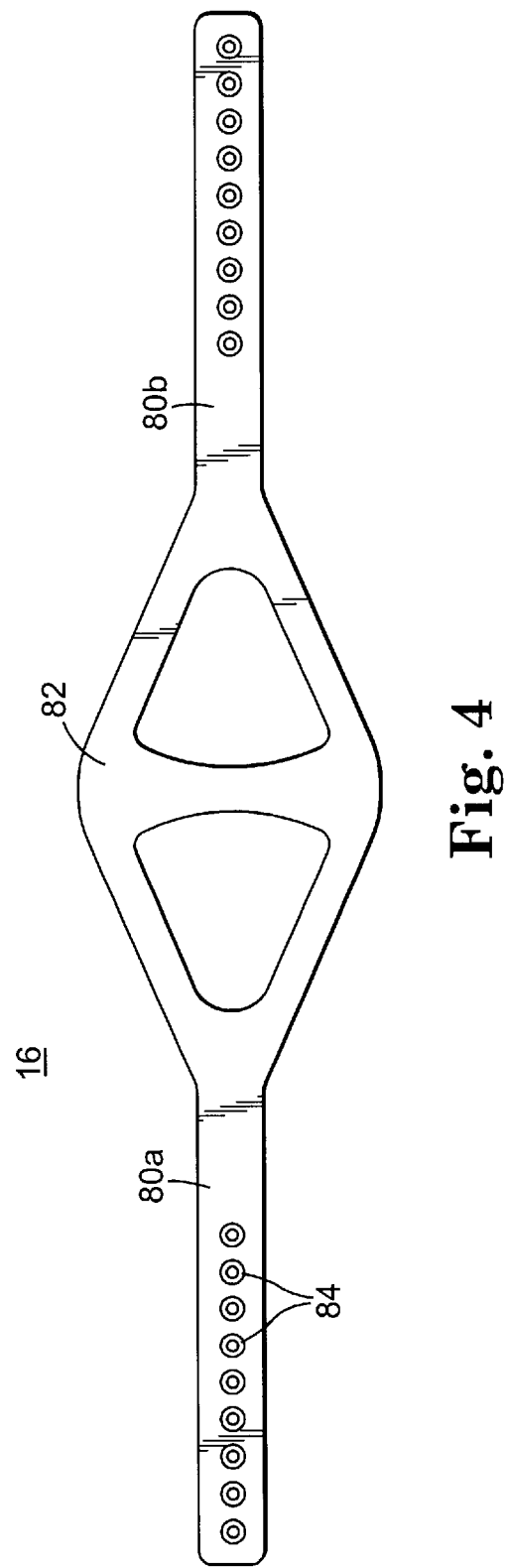
FIG. 4 illustrates a strap portion of the headframe of FIG. 1.

The strap 16 is shown in greater detail in FIG. 4. The strap 16 is preferably formed of an elastic material, preferably silicone, and includes strips 80a, 80b extending in an opposing fashion from a central region 82. As described below, the strap 16 is preferably sized for wrapping about a patient's head (not shown), and preferably has an overall length on the order of 21 inches. Each of the strips 80 forms holes 84, sized for coupling to a pin (not shown) otherwise mounted to a respective one of the swivel arms 14 (FIG. 3). The central region 82 preferably has an increased width relative to that of the strips 80, and is sized for placement over, or to straddle, the occipital bone. Alternatively, other configurations are equally acceptable.

Figure 5:
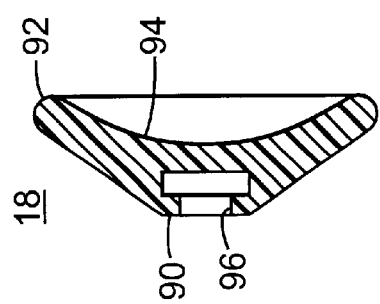
FIG. 5 is a cross-sectional view of a contact pad.

One of the contact pads 18 is shown in greater detail in FIG. 5. The contact pad 18 is preferably formed from a soft, autoclavable material, such as silicone, and defines an inner surface 90, a rim 92, and a contact surface 94. An opening 96 is formed through the inner surface 90 and is configured to receive a coupling device (not shown) for attachment to the frame body 12 (FIG. 2A). As described below, a ball joint or ball and socket device (not shown) is preferably used to pivotally couple the contact pad 18 to the frame body 12. In this regard, the opening 86 is sized to receive a portion of the coupling device in a manner that allows convenient disassembly therefrom, such that after use, the contact pad 18 can easily be removed and discarded or recycled, with the coupling device available for re-use following appropriate cleaning/sterilization. The rim 92 defines an outer diameter of the contact pad 18, preferably approximately 2 inches in diameter, it being understood that a wide variety of other dimensions, either greater or smaller, are equally acceptable. The contact surface 94 extends in a generally concave fashion from the rim 92. With this curved configuration, in conjunction with the durometer of the material selected for the contact pad 18, optimal comfort is provided to the patient, while providing maximum stability.

Figure 6:
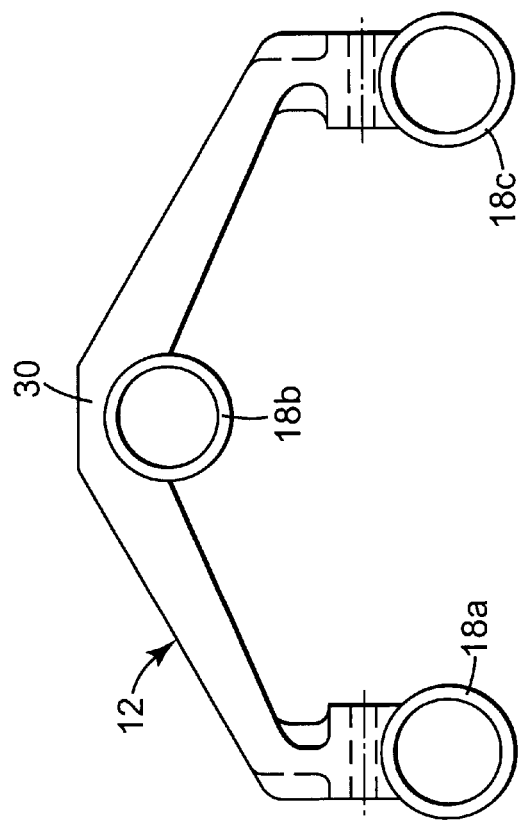
FIGS. 6 illustrates contact pads assembled to the frame body.

Assembly of the contact pads 18 to the frame body 12 is best shown in FIG. 6. As previously described, in a preferred embodiment three of the contact pads 18a–18c are provided and are secured to the central portion 30 and the opposing pad receiving regions 42, respectively. For example, in one preferred embodiment, a ball joint (not shown) is employed to mount a respective one of the contact pads 18a–18c to the frame body 12, with the ball portion being coupled to the transverse bores 46, 48 (FIG. 2C) otherwise formed by the frame body 12. With this one preferred mounting technique, each of the contact pads 18a–18c can be maneuvered or swiveled relative to the frame body 12 so as to accommodate a particular patient's head shape. Regardless of the exact mounting technique, the contact pads 18a–18c are arranged in a triangular or "tripod" fashion, with the contact pads 18a, 18c being equidistantly spaced from the contact pad 18b. This triangular arrangement of the contact pads 18a–18c provides greatly enhanced lateral stability relative to a two-pad design, thereby restricting overall motion of the individual contact pads 18.

Figure 7:
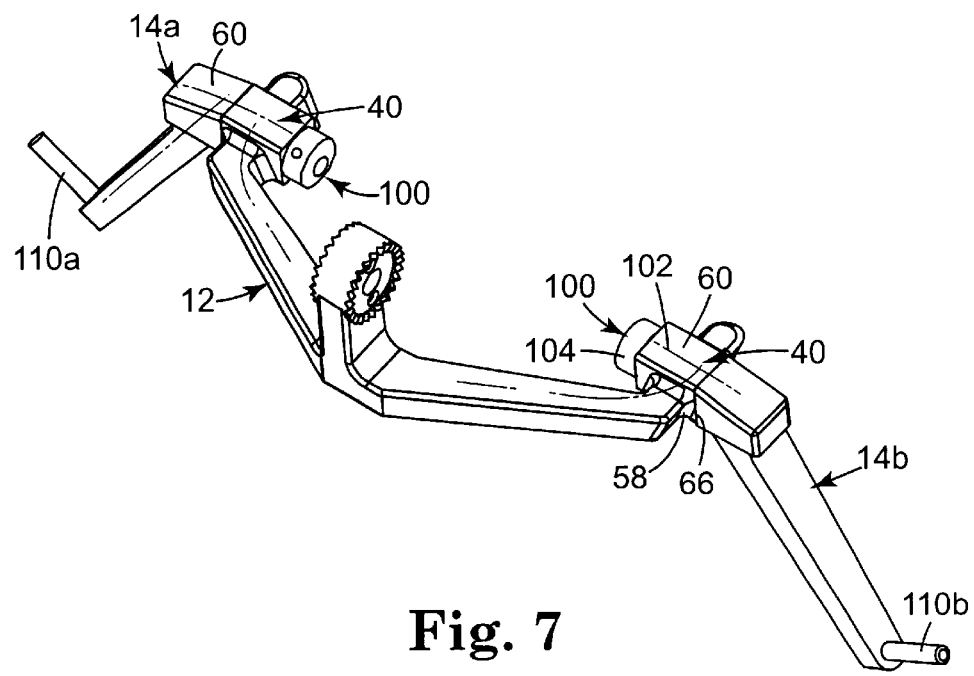
FIG. 7 illustrates assembly of the swivel arms to the frame body.

Assembly of the swivel arms 14 to the frame body 12 is shown in greater detail in FIG. 7. In particular, each of the swivel arms 14 is mounted to the frame body 12 by a coupling device 100 including a threaded pin 102 and a head 104. The pin 102 extends through the lateral passage 44 associated with the arm receiving region 40 of the frame body 12 and threadably engages the passage 68 formed in the base 60 of the respective swivel arm 14. The head 104 is preferably configured to provide convenient grasping by a surgeon who rotates the head 104 to thread the pin 102 into the base 60. Upon engagement by the coupling device 100, the inner face 66 of the swivel arm 14 abuts the engagement surface 58 of the arm receiving region 40. In this regard, the engagement surface 58 and the inner face 66 are preferably flat such that, where desired, the swivel arm 14 can freely rotate relative to the frame body 12 about the pin 102. More particularly, the swivel arms 14a, 14b are preferably assembled to allow for 360° movement relative to the frame body 12. During use, this preferred construction eliminates bending movements or forces from transferring from the step 16 (FIG. 1) through the respective pins 102 to the frame body 12 that might otherwise cause the headframe 10 (FIG. 1) to slip or move from a desired position. Finally, as a point of reference, the assembly of FIG. 7, depicts retention pins 110a, 110b extending from the leading ends 64 of the swivel arms 14a, 14b, respectively. As described below, the retention pins 110a, 110b are available for receiving and maintaining the strap 16.

Returning to FIG. 1, upon final assembly the surgical headframe 10 is secured to a patient's head 120 (preferably the forehead) by first locating the contact pads 18 against the head 120. As previously described, the concave nature of the contact pads 18 facilitates "gripping" of the contact pads 18 to the head 120. In the secured position, and as illustrated in FIG. 1, the swivel arms 14 extend rearwardly relative to the patient's head 120, substantially along the patient's temple, or slightly above the ears. The strap 16 is then wrapped behind the patient's head 120, much like a diving mask, and secured to the retention pins 110a, 110b via the holes 84. In one preferred embodiment, the central region 82 (FIG. 4) of the strap 16 is placed over the occilipate bone (not shown). Alternatively, other locations of the strap 16 relative to the patient's head 120 can be employed. Regardless, due to the elastic nature of the strap 16, the surgical headframe 10 can be tightly positioned or forced against the patient's head 120.

By employing ball joints 122 (shown partially in FIG. 1) to couple each of the contact pads 18 to the frame body 12, the contact pads 18 can swivel slightly to match the contours of the patient's head 120. Further, the triangular or tripod-like arrangement of the contact pads 18 renders the surgical headframe 10 highly stable relative to the patient's head 120. That is to say, the triangular orientation provides stability in all planes, and specifically prevents "rocking" of the headframe 10 along any one axis. Additionally, the contact pad 18b associated with the central portion 30 of the frame body 12 is offset from the plane in which the strap 16 wraps about the patient's head 120. As a result, the contact pad 18b effectively stretches the skin engaged by the contact pad 18b, further enhancing overall stability. Finally, the triangular or tripod arrangement of the contact pads 18 prevents skin between each of the contact pads 18 from stretching. This phenomenon is often times found with other nontraumatic headframe designs, and presents a distinct opportunity for undesirable headframe movement. Thus, movement problems associated with skin stretch found with other devices is eliminated with the tripod-like configuration of the present invention.

Figure 8:
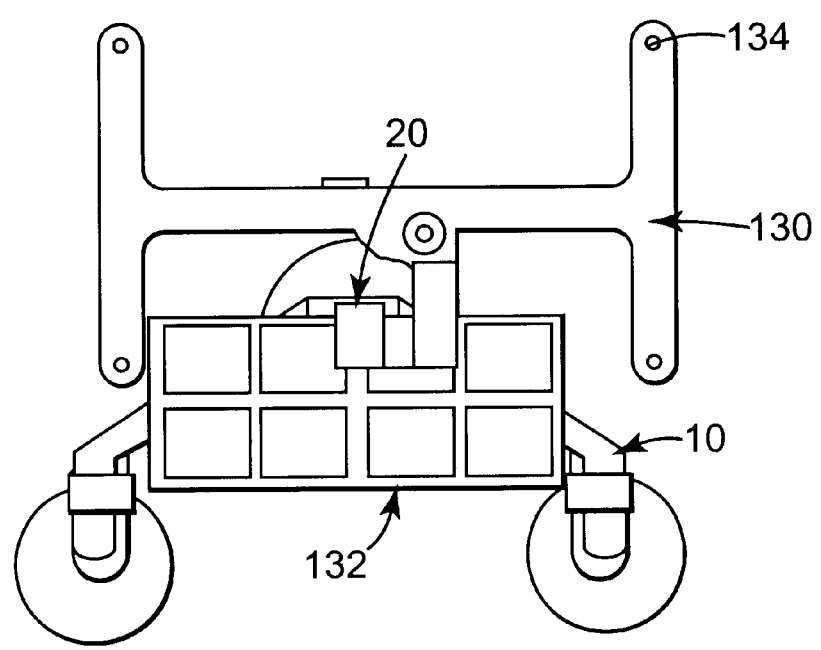
FIG. 8 illustrates auxiliary components assembled to the headframe of FIG. 1.

Once secured to the patient's head 120, the surgical headframe 10 is available for receiving and maintaining other components of the stereotactic system. In particular, a dynamic reference frame 130 and a touch pad 132 are preferably secured to the post 20 as shown in FIG. 8. As is known in the art, the dynamic reference frame 130 maintains one or more optical emitters 134 (shown generally in FIG. 8) that are utilized by the stereotactic system during surgical procedures. In this regard, the dynamic reference frame 130 is rigidly secured to the surgical headframe 10 via the post 20. As previously described, the surgical headframe 10 is fixed to the patient's head 120 (FIG. 1). Thus, the dynamic reference frame 130 is rigidly associated with the patient's head 120, and establishes a consistent reference zone even with movement of the patient's head 120. The touch pad 132 is an auxiliary device available to provide the surgeon with the ability to effectuate changes in the use/display of the stereotactic system. It should be understood, however, that the touch pad 132 is not a required element of the present invention, and can be secured to areas other than the post 20.

The surgical headframe of the present invention provides a marked improvement over previous designs. Fixation of the surgical headframe to a patient's head is non-invasive as it does not entail the use of bone screws or other incisions through the patient's skin. Further, as compared to clamp-type headframe designs, use of soft contact pads against the patient's skin greatly reduces the opportunity for trauma. Finally, by preferably orientating three contact pads in a triangular or tripod configuration, the headframe is highly stable in all dimensions.

Although the present invention has been described with reference to preferred embodiments, workers skilled in the art will recognize that changes can be made in form and detail without departing from the spirit and scope of the present invention. For example, while the surgical headframe has been described as preferably employing three contact pads, a two-contact pad design can also be employed. With this configuration, the head frame assumes a semi-circular arc conforming to a patient's forehead and includes a mounting lug for maintaining the dynamic reference frame. The head frame rests on the patient's forehead on the two-curved, swiveling pin-jointed contact pads and is held in place by way of an elastic strap. Further, while preferred dimensions have been ascribed to the various components, other dimensions, either greater or smaller, are equally acceptable.

Additionally, the frame body and swivel arms need not be made from aluminum. Instead, a wide variety of other materials are available. In fact, in accordance with an alternative embodiment, the frame body and swivel arms (as well as other components of the headframe) are formed of a non-magnetic material such as plastic, ceramic, or other composite such that the headframe is compatible with MRI, CT, X-ray and magnetic stereotactic devices/procedures.

What is claimed is:

1. A surgical headframe for maintaining a stereotactic system reference frame relative to a patient's head, the headframe comprising:
   a frame body defining a first and second arm receiving portion, the first arm receiving portion positioned opposite the second arm receiving portion;
   first and second arms extending from and being rotatable about the first and second arm receiving portions of the frame body, respectively; allowing an angle of the arms relative to the receiving portions to be adjusted
   a plurality of contact pads coupled to the frame body, the contact pads adapted to engage a patient's head; and
   a strap connectible to the first and second arms, the strap adapted for wrapping about a back of a patient's head;
   wherein the headframe is adapted to receive and maintain a stereotactic reference frame.

2. The headframe of claim 1, wherein the plurality of contact pads includes first, second and third contact pads.

3. The headframe of claim 2, wherein the first contact pad is coupled to a central portion of the frame body, and the second and third contact pads are positioned opposite one another relative to the first contact pad.

4. The headframe of claim 3, wherein the second and third contact pads are equidistantly spaced from the first contact pad.

5. The headframe of claim 3, wherein an arrangement of the first, second, and third contact pads defines a tripod.

6. The headframe of claim 3, wherein a center point spacing between the second and third contact pads is 4.125 inches.

7. The headframe of claim 3, wherein a lateral, center point spacing between the first and second contact pacts is 2.25 inches.

8. The headframe of claim 1, wherein each of the contact pads are pivotally coupled to the frame body.

9. The headframe of claim 1, wherein each of the contact pads defines a contact surface adapted for contacting a patient's head, and further wherein the contact pads are arranged such that the respective contact surfaces are co-planer.

10. The headframe of claim 1, wherein each of the contact pads has an outer diameter of approximately 2 inches.

11. The headframe of claim 1, wherein each of the contact pads defines a concave contact surface adapted for contacting a patient's bead.

12. The headframe of claim 1, wherein the first and second arms each include:
   a base defining an inner face for contacting a corresponding surface of the frame body;
   an intermediate section extending from the base, wherein extension of the intermediate section is non-planer relative to the inner face; and
   a leading end extending from the intermediate section opposite the base.

13. The headframe of claim 12, wherein the inner face defines an acute angle relative to a plane of the intermediate section.

14. The headframe of claim 12, wherein the inner face is flat.

15. The headframe of claim 12, wherein the base forms a transverse passage for receiving a mounting device that rotatably couples the respective arm to the frame body.

16. The headframe of claim 12, wherein the intermediate section forms opposing shoulders each adapted for receiving an auxiliary component.

17. The headframe of claim 12, wherein each of the first and second arms further includes a pin for retaining a portion of the strap.

18. The headframe of claim 17, wherein the pin extends from the leading end.

19. The headframe of claim 1, wherein the frame body includes:
   a central portion;
   a first leg; and
   a second leg;
   wherein the first and second legs extend in opposite directions from the central portion.

20. The headframe of claim 19, wherein the central portion, the first leg and the second leg combine to define a planer inner surface adapted for coupling to the contact pads.

21. The headframe of claim 19, wherein each of the central portion, the first leg, and the second leg are adapted to maintain a respective one of the contact pads.

22. The headframe of claim 19, wherein the first and second legs are symmetrically arranged relative to the central portion.

23. The headframe of claim 19, wherein each of the central portion, the first leg, and the second leg form a bore adapted for receiving a contact pad coupling device, and further wherein the bores of the first and second legs are equidistantly spaced from the bore of the central portion.

24. The headframe of claim 19, wherein each of the first and second legs includes:
   a first section extending in an angular fashion from the central portion; and
   a second section extending downwardly from the first section.

25. The headframe of claim 24, wherein the second section defines;
one of the arm receiving portions adapted to maintain a respective one of the first and second arms; and
a pad receiving portion adapted to maintain a respective one of the contact pads.

26. The headframe of claim 25, wherein the arm receiving portion includes a flat engagement surface for abutting a corresponding surface of a respective one of the first and second arms.

27. The headframe of claim 19, wherein a respective one of the contact pads extends from an inner surface of the central portion, the frame body further including a post extending from the central portion opposite the inner surface, the post being adapted to receive the reference frame.

28. The headframe of claim 1, wherein the strap includes:
a central region;
a first strip; and
a second strip;
wherein the first and second strips extend in an opposing fashion from the central region.

29. The headframe of claim 28, wherein each of the strips forms a plurality of holes adapted for selectively coupling the respective strip to a respective one of the arms.

30. The headframe of claim 28, wherein the central region is adapted for placement over an occipital bone of a patient's head.

31. The headframe of claim 1, further comprising;
a control pad adapted to facilitate control over a stereotactic procedure, the control pad being mounted to the frame body.

32. A method of manufacturing a surgical headframe for use in a stereotactic procedure, the method comprising:
providing a frame body including a central portion and opposing sides;
extending first and second arms from the opposing sides of the flame body, respectively;
coupling first, second and third contact pads to the frame body, the contact pads each adapted to engage a patient's head, the first contact pad being coupled to the central portion, and the second and third contact pads being positioned opposite one another relative to the first contact pad; and
selectively securing a strap to the first and second arms opposite die frame body, the strap adapted for wrapping about a back of a patient's head;
wherein the headframe is adapted to receive and maintain a stereotactic reference frame.

33. The method of claim 32, wherein coupling the contact pads to the frame body includes locating the first, second and third contact pads in a tripod arrangement.

34. The method of claim 32, wherein coupling the contact pads includes pivotally mounting at least one of the contact pads to the frame body.

35. The method of claim 32, wherein extending the first and second arms from the frame body includes rotatably mounting each of the arms to the frame body.

36. The method of claim 32, wherein selectively securing a strap to the first and second arms includes:
providing the strap with a plurality of holes; and
extending a pin from each of the arms, respectively;
wherein the holes are sized to be received over the respective pins.

37. The method of claim 32, further comprising:
providing the frame body with a post adapted to receive a stereotactic reference frame.

38. The method of claim 32, further comprising:
mounting a control pad to the frame body, the control pad adapted to facilitate control over a stereotactic procedure.

39. A surgical headframe for maintaining a stereotactic system reference frame relative to a patient's head, the headframe comprising:
a frame body;
first and second arms extending from opposing sides of the frame body, respectively;
a plurality of contact pads pivotally coupled to the frame body, the contact pads adapted to engage the patient's head; and
a strap connectible to the first and second arms, the strap adapted for wrapping about a back of the patient's head;
wherein the headframe is adapted to receive and maintain a stereotactic reference frame.

40. A surgical headframe for maintaining a stereotactic system reference frame relative to a patient's head, the headframe comprising:
a frame body;
first and second arms extending from opposing sides of the frame body, respectively;
a plurality of contact pads coupled to the frame body, the contact pads adapted to engage the patient's head, each of the contact pads defining a contact surface adapted for contacting the patient's head, the contact pads being arranged such that the respective contact surfaces are co-planer; and
a strap connectible to the first and second arms, the strap adapted for wrapping about a back of the patient's head;
wherein the headframe is adapted to receive and maintain a stereotactic reference frame.

41. A surgical headframe for maintaining a stereotactic system reference frame relative to a patient's head, the headframe comprising:
a frame body;
first and second arms extending from opposing sides of the frame body, respectively;
a plurality of contact pads coupled to the frame body, the contact pads adapted to engage the patient's head, each of the contact pads defining a concave contact surface adapted for contacting the patient's head; and
a strap connectible to the first and second arms, the strap adapted for wrapping about a back of the patient's head;
wherein the headframe is adapted to receive and maintain a stereotactic reference frame.

42. A surgical headframe for maintaining a stereotactic system reference frame relative to a patient's head, the headframe comprising;
a frame body;
first and second arms extending from opposing sides of the frame body, respectively, each of the first and second arms include:
a base defining an inner face for contacting a corresponding surface of the frame body, and
an intermediate section extending from the base, wherein a plane of the intermediate section defines an acute angle relative to the inner face;

a plurality of contact pads coupled to the frame body, the contact pads adapted to engage the patient's head; and a strap connectible to the first and second arms, the strap adapted for wrapping about a back of the patient's head;

wherein the headframe is adapted to receive and maintain a stereotactic reference frame.

43. A surgical headframe for maintaining a stereotactic system reference frame relative to a patient's head, the headframe comprising:

a frame body, first and second arms extending from opposing sides of the frame body, respectively, the first and second arms each including a base for contacting a corresponding surface of the frame body, the base forming a transverse passage for receiving a mounting device that rotatably couples the respective arm to the frame body;

a plurality of contact pads coupled to the frame body, the contact pads adapted to engage the patient's head; and a strap connectible to the first and second arms, the strap adapted for wrapping about a back of the patient's head;

wherein the headframe is adapted to receive and maintain a stereotactic reference frame.

44. A surgical headframe for maintaining a stereotactic system reference frame relative to a patient's head, the headframe comprising:

a frame body;

first and second arms extending from opposing sides of the frame body, respectively, the first and second arms each including a pin;

a plurality of contact pads coupled to the frame body, the contact pads adapted to engage the patient's head; and a strap adapted for wrapping about a back of the patient's head;

wherein the pins of the first and second arms each retains a portion of the strap, and the headframe is adapted to receive and maintain a stereotactic reference frame.

45. A surgical headframe for maintaining a stereotactic system reference frame relative to a patent's head, the headframe comprising:

a frame body including:

a central portion, a first leg extending from the central portion, and a second leg extending form the central portion in the opposite direction as the first leg, wherein each of the central portion, the first leg, and the second leg form a bore adapted for receiving a contact pad coupling device;

first and second arms extending from opposing sides of the frame body, respectively;

a plurality of contact pads coupled to the frame body, the contact pads adapted to engage the patient's head; and a strap connectible to the first and second arms, the strap adapted for wrapping about a back of the patient's head;

wherein the headframe is adapted to receive and maintain a stereotactic reference frame.

46. A surgical headframe for maintaining a stereotactic system reference frame relative to a patient's head, the headframe comprising:

a frame body including:

a central portion, and first and second legs extending in opposite directions from the central portion, wherein each leg defines an arm receiving portion, which is adapted to maintain a respective one of the first and second arm, and a pad receiving portion, which is adapted to maintain a respective one of the contact pads;

first and second arms extending from opposing sides of the frame body, respectively;

a plurality of contact pads coupled to the frame body, the contact pads adapted to engage the patient's head; and a strap connectible to the first and second arms, the strap adapted for wrapping about a back of the patient's head;

wherein the headframe is adapted to receive and maintain a stereotactic reference frame.

47. A surgical headframe for maintaining a stereotactic system reference frame relative to a patient's head, the headframe comprising:

a frame body including a central portion, which defines an inner surface, and a post adapted to receive the reference frame, the post extending from the central portion opposite the inner surface;

first and second arms extending from opposing sides of the frame body, respectively;

a plurality of contact pads coupled to the frame body, the contact pads adapted to engage the patient's head, a respective one of the contact pads extending from the inner surface of the central portion; and a strap connectible to the first and second arms, the strap adapted for wrapping about a back of the patient's head;

wherein the headframe is adapted to receive and maintain a stereotactic reference frame.

48. A surgical headframe for maintaining a stereotactic system reference frame relative to a patient's head, the headframe comprising:

a frame body;

first and second arms extending from opposing sides of the frame body, respectively;

a plurality of contact pads coupled to the frame body, the contact pads adapted to engage the patient's head; and a strap adapted for wrapping about a back of the patient's head, the strap including:

a central region, a first strip, and a second strip, the first and second strips extending in an opposing fashion from the central region, wherein each of the strips forms a plurality of holes adapted for selectively coupling the respective strip to a respective one of the arms;

wherein the headframe is adapted to receive and maintain a stereotactic reference frame.

49. A surgical headframe for maintaining a stereotactic system reference frame relative to a patient's head, the headframe comprising:

a frame body;

first and second arms extending from opposing sides of the frame body, respectively, a plurality of contact pads coupled to the frame body, the contact pads adapted to engage the patient's head;

a strap connectible to the first mid second arms, the strap adapted for wrapping about a back of the patient's head; and a control pad adapted to facilitate control over a stereotactic procedure, the control pad being mounted to the frame body;

wherein the headframe is adapted to receive and maintain a stereotactic reference frame.

* * * * *

UNITED STATES PATENT AND TRADEMARK OFFICE
CERTIFICATE OF CORRECTION

PATENT NO. : 6,770,082 B2 Page 1 of 1
DATED : August 3, 2004
INVENTOR(S) : Leonel Dominguez et al.

It is certified that error appears in the above-identified patent and that said Letters Patent is hereby corrected as shown below:

<u>Title page,</u>
Item [57], ABSTRACT,
Line 12, after "patient's head", please delete "daring" and insert -- during --.

Signed and Sealed this

Ninth Day of November, 2004

JON W. DUDAS
*Director of the United States Patent and Trademark Office*